United States Patent
Rakos et al.

(10) Patent No.: US 8,343,207 B2
(45) Date of Patent: *Jan. 1, 2013

(54) COMPOSITE MEDICAL TEXTILE MATERIAL AND IMPLANTABLE DEVICES MADE THEREFROM

(76) Inventors: Ronald Rakos, Neshanic Station, NJ (US); Krzysztof Sowinski, Wallington, NJ (US)

( * ) Notice: Subject to any disclaimer, the term of this patent is extended or adjusted under 35 U.S.C. 154(b) by 375 days.

This patent is subject to a terminal disclaimer.

(21) Appl. No.: 12/694,080

(22) Filed: Jan. 26, 2010

(65) Prior Publication Data

US 2010/0137969 A1  Jun. 3, 2010

Related U.S. Application Data

(62) Division of application No. 10/830,787, filed on Apr. 23, 2004.

(51) Int. Cl.
*A61F 2/06* (2006.01)
*A61M 29/00* (2006.01)

(52) U.S. Cl. ...................... 623/1.13; 606/198

(58) Field of Classification Search ............... 623/1.11, 623/1.12, 1.13, 1.14, 1.15, 1.23
See application file for complete search history.

(56) References Cited

U.S. PATENT DOCUMENTS

| | | |
|---|---|---|
| 3,105,492 A | 10/1963 | Jeckel |
| 3,108,357 A | 10/1963 | Liebig |
| 3,316,557 A | 5/1967 | Liebig |
| 3,853,462 A | 12/1974 | Smith |
| 3,986,828 A | 10/1976 | Hoffman, Jr. et al. |
| 4,304,010 A | 12/1981 | Mano |
| 4,503,569 A | 3/1985 | Dotter |
| 4,580,568 A | 4/1986 | Gianturco |
| 4,732,152 A | 3/1988 | Wallsten et al. |
| 4,733,665 A | 3/1988 | Palmaz |
| 4,856,516 A | 8/1989 | Hillstead |
| 5,061,276 A | 10/1991 | Tu et al. |
| 5,178,630 A | 1/1993 | Schmitt |
| 5,192,310 A | 3/1993 | Herweck et al. |
| 5,209,776 A | 5/1993 | Bass et al. |
| 5,653,746 A | 8/1997 | Schmitt |
| 5,693,088 A * | 12/1997 | Lazarus ............... 623/1.35 |
| 5,741,332 A | 4/1998 | Schmitt |
| 5,800,512 A | 9/1998 | Lentz et al. |
| 5,851,229 A | 12/1998 | Lentz et al. |

(Continued)

FOREIGN PATENT DOCUMENTS

WO    95/25482    9/1995

(Continued)

*Primary Examiner* — Vy Q Bui
(74) *Attorney, Agent, or Firm* — Vidas, Arrett & Steinkraus, P.A.

(57) ABSTRACT

An implantable composite medical device having a longitudinal length a woven textile portion having yarns interlaced in a woven pattern, a knitted textile portion having yarns interlooped in a knitted pattern. The woven and knitted portions are securably attached to one and the other to provide a composite woven and knitted textile surface along the longitudinal length of the device. The woven portion may have a permeability from about 30 to about 500 ml/min/cm$^2$, and the knitted portion may have a permeability from about 30 to about 15,000 ml/min/cm$^2$. Further, a crimped woven portion with a resiliently longitudinal stretchability from about 10 to about 100 linear percent over its quiescent longitudinal dimension or an uncrimped woven portion with a resiliently longitudinal stretchability of less than about 10 linear percent over its quiescent longitudinal dimension are useful. A knitted portion with a resiliently longitudinal stretchability from about 5 to about 200 linear percent over its quiescent longitudinal dimension is also useful.

6 Claims, 14 Drawing Sheets

U.S. PATENT DOCUMENTS

| | | | |
|---|---|---|---|
| 5,886,062 A | 3/1999 | Dietrich et al. | |
| 5,976,196 A | 11/1999 | Cooper et al. | |
| 6,001,125 A | 12/1999 | Golds et al. | |
| 6,036,724 A | 3/2000 | Lentz et al. | |
| 6,080,198 A | 6/2000 | Lentz et al. | |
| 6,090,137 A | 7/2000 | Schmitt | |
| 6,156,064 A * | 12/2000 | Chouinard | 623/1.44 |
| 6,221,099 B1 * | 4/2001 | Andersen et al. | 623/1.15 |
| 6,325,822 B1 | 12/2001 | Chouinard et al. | |
| 6,428,571 B1 | 8/2002 | Lentz et al. | |
| 6,540,773 B2 | 4/2003 | Dong | |
| 6,547,820 B1 | 4/2003 | Staudenmeier | |
| 6,554,855 B1 | 4/2003 | Dong | |
| 6,585,758 B1 | 7/2003 | Chouinard et al. | |
| 6,716,239 B2 | 4/2004 | Sowinski et al. | |
| 6,719,783 B2 | 4/2004 | Lentz et al. | |
| 6,814,754 B2 * | 11/2004 | Greenhalgh | 623/1.51 |
| 7,105,021 B2 * | 9/2006 | Edens et al. | 623/1.5 |
| 7,682,381 B2 | 3/2010 | Rakos et al. | |
| 2003/0009210 A1 | 1/2003 | Sowinski et al. | |
| 2003/0017775 A1 | 1/2003 | Sowinski et al. | |
| 2003/0139806 A1 | 7/2003 | Haverkost et al. | |
| 2003/0204241 A1 | 10/2003 | Dong | |

FOREIGN PATENT DOCUMENTS

| | | |
|---|---|---|
| WO | 02/35989 | 5/2002 |

* cited by examiner

COMPOSITE MEDICAL TEXTILE MATERIAL AND IMPLANTABLE DEVICES MADE THEREFROM

CROSS-REFERENCE TO RELATED APPLICATONS

This application is a Division of U.S. application Ser. No. 10/830,787, filed Apr. 23, 2004, the entire contents of which are hereby incorporated herein by reference.

FIELD OF INVENTION

The present invention is directed to a composite textile medical material having at least two different textile patterns and implantable devices made therefrom.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion, dissection or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract, tracheal/bronchial tubes and bile duct, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten and U.S. Pat. No. 4,886,062 to Wiktor, all of whose contents are incorporated herein by reference.

A graft is another commonly known type of intraluminal prosthesis which is used to repair and replace various body vessels. A graft provides a lumen through which blood may flow. Moreover, a graft is often configured to have porosity to permit the ingrowth of cells for stabilization of an implanted graft while also being generally impermeable to blood to inhibit substantial leakage of blood therethrough. Grafts are typically tubular devices which may be formed of a variety of materials, including textile and non-textile materials.

Grafts may be flexible to provide compliance within a bodily lumen or within the bodily system. Such flexibility may result from the stretching of the textile yarns that form the graft. Such stretching, however, may effect the securement of the graft to the bodily lumen, which is typically secured by the use of sutures. In other words, the graft flexibility may create undesirable stresses at the suture locations of the implanted graft.

A stent and a graft may be combined to form an intraluminal device, such as a stent-graft, which may dilate over time after implantation within a bodily lumen. The dilation of the implanted intraluminal device is a radial enlargement of the device resulting from pulsating stresses or pressures present within the bodily lumen. The actions of the pulsating stresses or pressures often fatigue the structure of the device resulting in radial expansion and possibly longitudinal foreshortening.

Thus, there is a need for graft having improved compliance by reducing potential stresses at locations where the graft is secured to a bodily lumen. Further, there is a need for a prosthesis having improved resistance to dilation.

SUMMARY OF THE INVENTION

The present invention provides a graft or graft/composite implantable device having improved compliance and/or improved resistance to dilation by providing different textile portions which advantageously have different, but desirable, mechanical properties.

In one aspect of the present invention an implantable composite medical device having a longitudinal length is provided. The device includes a woven textile portion having yarns interlaced in a woven pattern; a knitted textile portion having yarns interlooped in a knitted pattern; and an attachment means for securing the woven and the knitted textile portions to provide a composite woven and knitted textile surface along the longitudinal length. Desirably, the woven portion has a permeability from about 30 to about 500 ml/min/cm$^2$, and the knitted portion has a permeability from about 30 to about 15,000 ml/min/cm$^2$. A knitted portion with a permeability from about 8,000 to about 12,000 ml/min/cm$^2$ is also useful. Further, a woven portion, such as a crimped woven portion, with a resiliently longitudinal stretchability from about 10 to about 100 linear percent over its quiescent longitudinal dimension is useful. A woven portion, such as an uncrimped woven portion, with a resiliently longitudinal stretchability of less than about 10 linear percent is also useful. A knitted portion with a resiliently longitudinal stretchability from about 5 to about 200 linear percent over its quiescent longitudinal dimension is also useful.

The attachment means for securably attaching the two different textile portions may include yarns which are present in both the knitted and the woven portions; yarns or textile components which join the knitted and the woven portions; sutures; an adhesive bonding of the knitted and the woven portions; a heat-fusible bonding of the knitted and the woven portions; ultrasonic bonding of the knitted and the woven portions and combinations thereof.

The woven and knitted portions may be seamless tubular portions defining a cylindrical textile wall having an interior surface and an exterior surface and having opposed first and second textile open ends, defining an implantable graft. Desirably, the portions of the cylindrical textile wall proximal to the first and the second textile open ends are the woven portions and a transitional portion of the cylindrical textile wall between the woven portions is the knitted portion. The graft of this aspect of the present invention may also be crimped.

In another aspect of the present invention, an implantable graft is provided. The graft further includes a polymeric tube or layer circumferentially disposed about portions of the interior surface or about portions of the exterior surface of the textile wall; and a second attachment means for securing the polymeric tube or layer about portions of the interior surface or about portions of the exterior surface of the textile wall. The second attachment means may include adhesive bonding of the polymeric tube or layer about portions of the interior surface or about portions of the exterior surface of the textile wall. The implantable graft may be of straight or tapered configuration. Desirably, the polymeric tube or layer is polytetrafluoroethylene (PTFE) and more desirably expanded polytetrafluoroethylene (ePTFE). Such a tube or layer may be formed from an extruded tube, a sheet wrapped into a tubular structure, a helically wound ribbon of material, and the like. The graft of this aspect of the present invention may also be crimped along its length or just along portions of its length.

In another aspect of the present invention, the medical device of claim further includes a generally tubular stent having openings in its wall structure and having opposed first and second stent open ends, and a third attachment means for securing stent to portions of the interior or exterior surface of the textile wall to define a stent/graft prosthesis. Desirably, the stent is a radially distensible stent, such as a wire stent, including a braided wire stent. The third attachment means may include mechanical securement of the stent to portions of the interior or exterior surface of the textile wall or adhesive securement of the stent to portions of the interior or exterior surface of the textile wall.

The prosthesis of this aspect of the present invention may further include a polymeric tube or layer circumferentially disposed and securably attached by the third attachment means to the interior and/or exterior portions of the prosthesis. The third attachment means may include adhesive securement of the stent to portions of the interior or exterior surface of the textile wall. Desirably, the polymeric tube or layer is a PTFE or ePFTE tube or layer.

Desirably, the prosthesis of this aspect of the present invention has specific textile portions where portions of the cylindrical textile wall proximal to the first and the second opposed textile open ends are the woven portions and a transitional portion of the cylindrical textile wall between the opposed woven portions is the knitted portion. Further, the stent of this aspect of the present invention may have a varying diameter between the first and second stent open ends defining a transitional stent section therebetween; the textile wall may also have a varying diameter between the first and second textile open ends defining a transitional textile section therebetween with the transitional textile section being securable attached to the transitional stent section by the third attachment means; and where the transitional textile portion is the woven textile portion. Further, portions of the cylindrical textile wall proximal to the first and the second opposed textile open ends may be the woven portions and other portions of the cylindrical textile wall between the woven portions and the transitional textile portion are knitted portions.

In another aspect of the present invention, the prosthesis may further include a second tubular textile wall at the second textile open end to define a multi-lumen textile portion, the multi-lumen textile portion being secured by the attachment means to a transitional portion of the cylindrical textile wall which is secured by the attachment means to a portion of the cylindrical textile wall of the first textile open end; and a second tubular stent wall at the second stent open end to define a multi-lumen stent portion, the multi-lumen stent portion being secured to a transitional portion of the stent wall which is connected to the stent wall proximal to the first stent open end; wherein the multi-lumen stent portion is securably attached by the third attachment means to the multi-lumen textile portion to define a multi-lumen prosthesis. Desirably, the transitional portion of the cylindrical textile wall is the woven portion. More desirably, the transitional portion of the cylindrical textile wall is the woven portion, and the multi-lumen textile portion and the portion of the cylindrical textile wall of the first textile open end are knitted portions.

Useful woven patterns include a simple weave, a basket weave, a twill weave, a satin weave, a velour weave, a double velour weave, and combinations thereof. Useful knitted patterns include a locknit pattern, a reverse locknit pattern, a velour pattern, a double velour pattern, a high-stretch knit pattern having at least a two-needle underlap with a one-needle overlap, and combinations thereof. The woven and knitted textile portions may be single-layered textile portions.

In another aspect of the present invention, a composite textile graft is provided. The graft includes a seamless tubular knitted textile portion having yarns interlooped in a knitted pattern defining a cylindrical knitted textile wall having opposed open ends; a seamless tubular woven textile portion having yarns interlaced in a woven pattern defining a cylindrical woven textile wall having opposed open ends; and attachment means for securing one of the open ends of the woven textile portion to one of the open ends of the knitted textile portion. The graft may further include a second seamless tubular woven textile portion having yarns interlaced in a woven pattern defining a cylindrical woven textile wall having opposed open ends; wherein the second woven textile portion is securably attached by the attachment means to the other of the open ends of the knitted textile portion. Desirably, the woven portion has a permeability from about 30 to about 500 ml/min/cm$^2$, and the knitted portion has a permeability from about 30 to about 15,000 ml/min/cm$^2$. Also desirably, the woven portion is a crimped portion having a resiliently longitudinal stretchability from about 10 to about 100 linear percent over its quiescent longitudinal dimension or an uncrimped portion having a resiliently longitudinal stretchability of less than about 10 linear percent, and the knitted portion has a resiliently longitudinal stretchability from about 5 to about 200 linear percent over its quiescent longitudinal dimension. The graft may further include a polymeric tube or layer circumferentially disposed and securably attached about interior or exterior portions of the woven and the knitted textile walls.

In another aspect of the present invention a stent/graft prosthesis is provided. The stent/graft prosthesis includes a seamless tubular knitted textile portion having yarns interlooped in a knitted pattern defusing a cylindrical knitted textile wall having opposed first and second open ends; a first seamless tubular woven textile portion having yarns interlaced in a woven pattern defining a cylindrical woven textile wall having opposed open ends; an attachment means for securing the first open end of the first woven textile portion to the first open end of the knitted textile portion; a second seamless tubular woven textile portion having yarns interlaced in a woven pattern defining a cylindrical woven textile wall having opposed open ends, wherein the second woven textile portion is securably attached by the attachment means to the second open end of the knitted textile portion; a generally tubular stent having openings in its wall structure and having opposed first and second stent open ends, wherein the stent is circumferentially disposed about interior portions of the knitted textile and the woven textile walls; and a second attachment means for securing the stent about interior portions of the knitted textile and the woven textile walls. Desirably, the woven portions have a permeability from about 30 to about 500 ml/min/cm$^2$ and the knitted portion has a permeability from about 30 to about 15,000 ml/min/cm$^2$. Also desirably, the woven portions may be crimped to provide resiliently longitudinal stretchability from about 10 to about 100 linear percent over its quiescent longitudinal dimension, or uncrimped with a resiliently longitudinal stretchability of less than about 10 linear percent, and the knitted portion has a resiliently longitudinal stretchability from about 5 to about 200 linear percent over its quiescent longitudinal dimension. The prosthesis may further include a polymeric tube or layer circumferentially disposed and securably attached by the second attachment means about interior portions of the woven and the knitted textile walls. Desirably, the stent is a radially distensible stent.

In another aspect of the present invention another stent/graft prosthesis is provided. This stent/graft prosthesis includes a generally tubular stent having openings in its wall structure and having opposed first and second stent open ends, wherein a diameter of the first stent open end is different from a diameter of the second stent open end thereby defining a transitional stent portion therebetween stent portions proximal to the first and the second stent open ends; a seamless tubular woven textile portion having yarns interlaced in a woven pattern defining a cylindrical woven textile wall having an interior surface, an exterior surface and opposed open ends; attachment means for securing the woven textile portion to interior and/or exterior portions of the transitional stent portion; and first and second seamless tubular knitted textile portions having yarns interlooped in a knitted pattern defining cylindrical knitted textile walls having interior surfaces, exterior surfaces and opposed open ends, wherein the first knitted textile portion is securably attached by the attachment means to interior and/or exterior portions of the stent portion proximal to the first stent open end and the second knitted textile portion is securably attached by the attachment means to interior and/or exterior portions of the stent portion proximal to the second stent open end the. The woven portion may have a permeability from about 30 to about 500 ml/min/cm$^2$ and the knitted portion may have a permeability from about 30 to about 15,000 ml/min/cm$^2$. Further, the woven portion may have a resiliently longitudinal stretchability from about 10 to about 100 linear percent or less than about 10 linear percent over its quiescent longitudinal dimension, and the knitted portions may have a resiliently longitudinal stretchability from about 5 to about 200 linear percent over its quiescent longitudinal dimension.

This prosthesis may further include a polymeric tube or layer circumferentially disposed about interior and/or exterior portions of the prosthesis; and second attachment means for securing the polymeric tube or layer about the interior and/or the exterior portions of the prosthesis. This prosthesis may further a third attachment means for securing the knitted textile portions to the woven portion.

In another aspect of the present invention, a bifurcated stent-graft is provided where the main tubular textile portion is a woven textile and the tubular textile legs are knitted portions. The stents for the different portions of the bifurcated device may be the same or different in design. Desirably, the stent for the main tubular prosthesis is a balloon-expandable stent, and the stents for the legs are braided self-expanding stents.

DETAILED DESCRIPTION OF THE INVENTION

The present invention is an implantable medical device having a composite textile construction defined by at least two textile portions with substantially different textile porosity or permeability. The permeability variation is achieved by the use of different textile patterns; such as woven or knitted patterns; different yarn types, and different post textile processing, such as compaction.

Figure 1:
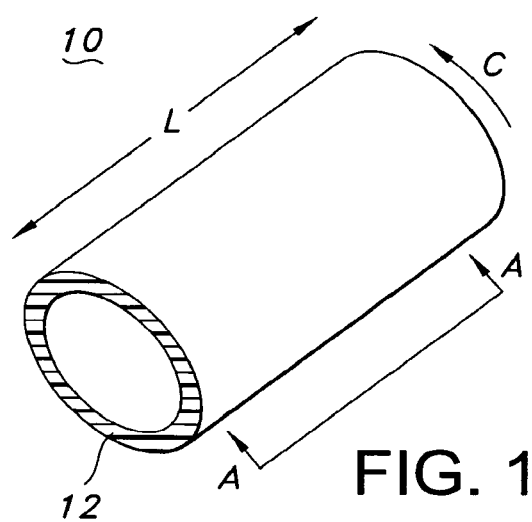
FIG. 1 is a perspective view of a tubular prosthesis of the present invention.

The composite textile medical device of the present invention may be a hollow tubular prosthesis 10, as illustrated in FIG. 1. The prosthesis 10 is a single lumen device defined by a cylindrical wall 12. The cylindrical wall 12 of prosthesis 10 includes the composite textile construction of the present invention and may further include a polymeric tube or film-like tube associated with it to provide a composite textile/polymeric prosthesis. Further, the composite textile prosthesis and the composite textile/polymeric prosthesis may have a stent associated with it to provide a stent/graft device.

Figure 3:
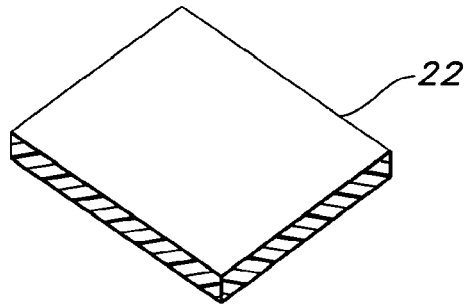
FIG. 3 is a perspective view of an implantable patch of the present invention.
Figure 2:
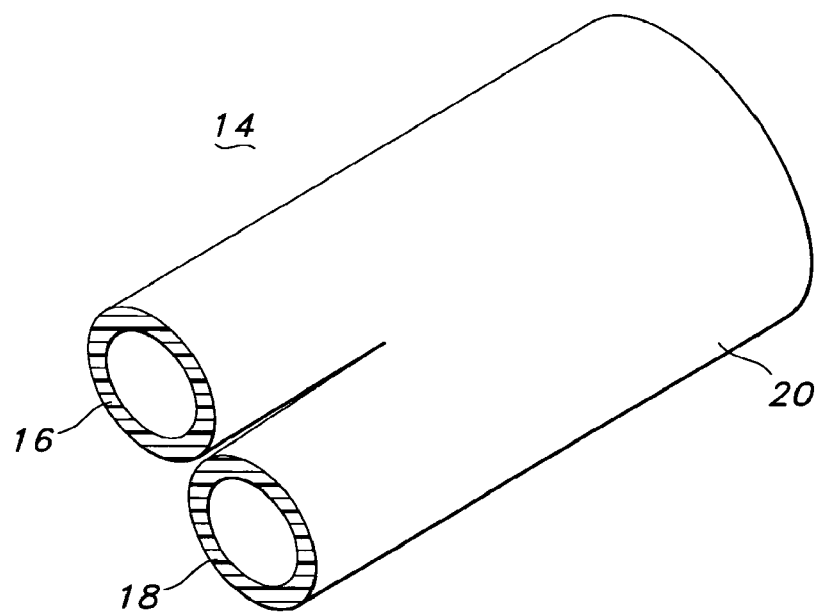
FIG. 2 is a perspective view of a bifurcated tubular prosthesis of the present invention.

The present invention, however, is not limited to composite textile constructions of single lumen construction. For example, a multi-lumen prosthesis, such as bifurcated prosthesis 14, may suitably be provided with a composite textile construction. As depicted in FIG. 2, bifurcated prosthesis 14 includes two hollow tubular legs 16, 18 and a main hollow tubular body 20. Further, the present invention is not limited to tubular prostheses, and non-tubular medical devices may suitably contain composite textile constructions of the present invention. For example, as depicted in FIG. 3, a medical patch 22 may be formed as a composite medical device. Although medical patch 22 is depicted as a square, other non-limiting shapes may suitably be used. Such other non-limiting shapes include oval, circular, rectangular, triangular, polygonal and non-polygonal shapes.

Figure 4:
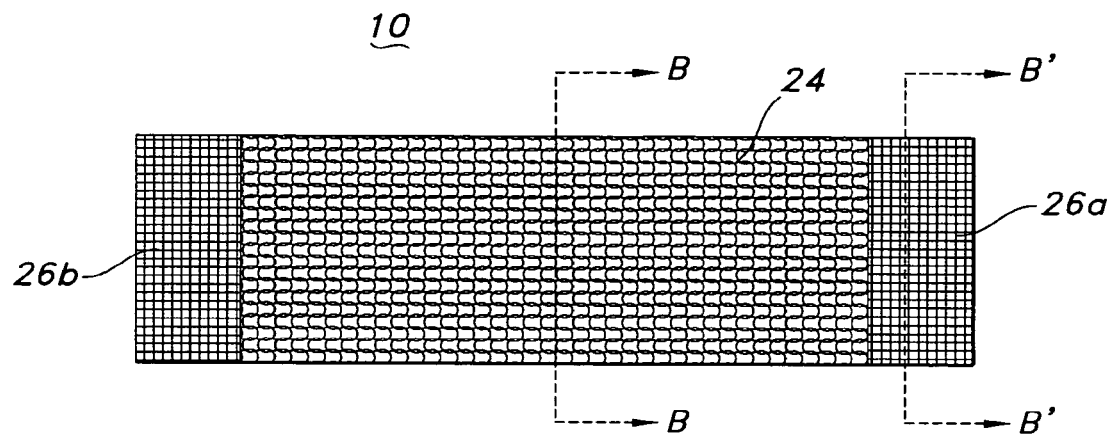
FIG. 4 is side longitudinal view of the prosthesis of FIG. 1 taken along the A-A axis depicting a prosthesis having a composite textile surface with a first textile portion disposed between terminal second textile portions.

A side longitudinal view of the prosthesis 10 of FIG. 1 taken along the A-A axis is depicted in FIG. 4. As depicted in FIG. 4, prosthesis 10 includes a first textile portion 24 and second textile portions 26a, 26b. The textile portions 26a, 26b, which may be the same or different, are depicted as having a lower permeability and/or stretchability, as compared to the first textile portion. Desirably, first textile portion 24 is a knitted textile portion. Second textile portions 26a, 26b are desirably woven textile portions.

The second textile portions 26a, 26b advantageously aid in securing prosthesis 10 to bodily lumens. For example, when second textile portions 26a, 26b are woven portions, sutures which secure the prosthesis 10 to a bodily lumen (not shown) are more readily secured within the woven pattern as compared to other more resilient textile patterns, such as knitted or braided patterns. The second textile portions 26a, 26b are depicted as being minor portions proximally located at the ends of the prosthesis 10. The present invention, however, is not so limited.

Figure 5:
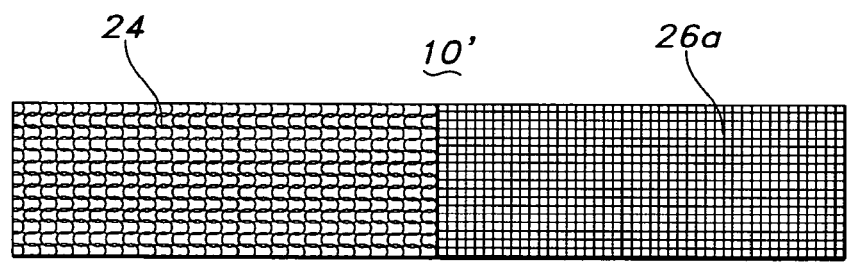
FIG. 5 is a side longitudinal view of a second embodiment of the prosthesis of FIG. 1 taken along the A-A axis depicting a prosthesis having a composite textile surface with a first and a second textile portion.

As depicted in FIG. 5, prosthesis 10' is a composite textile having significant portions formed from different textile patterns. Prosthesis 10' includes a first textile portion 24, which is desirably a knitted textile portion, and a second textile portion 26a, which is desirably a woven textile portion. Although prosthesis 10' is depicted as having about 50 percent textile portion 24 and about 50 percent textile portion 26a, the present invention is not so limited. For example, prosthesis 10' may include from about 5 to 95 percent textile portion 24 and from about 95 to 5 percent textile portion 26a, where the percents are based on the longitudinal length of the overall prosthesis 10'.

Figure 6:
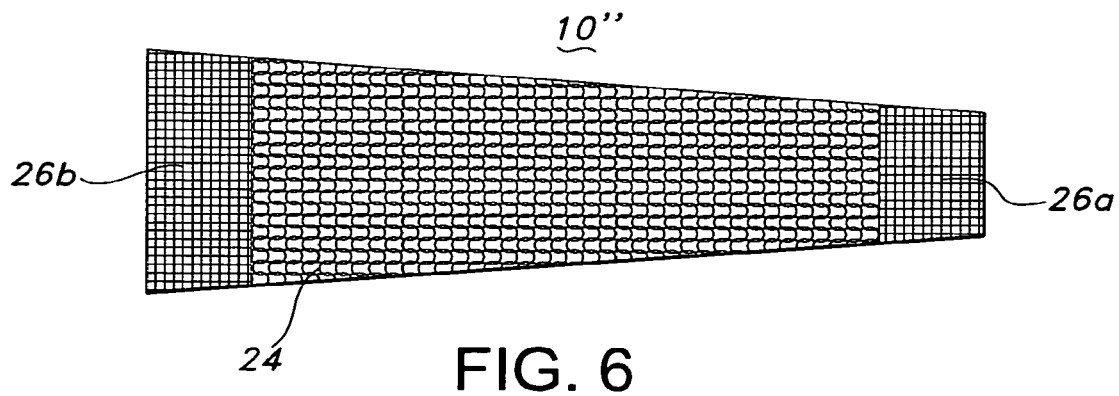
FIG. 6 is a side longitudinal view of yet another embodiment of the prosthesis of FIG. 1 taken along the A-A axis depicting a flared prosthesis with composite textile surface having a first textile portion disposed between terminal second textile portions.

Further, as depicted in FIG. 6, the composite textile prosthesis 10" of the present invention is not limited to substantially straight tubular devices as depicted in FIGS. 4 and 5. Prosthesis 10" may have a varying diameter, such as a tapered shape as shown in FIG. 6. Although prosthesis 10" is depicted as a first textile portion 24 and second textile portions 26a, 26b at both ends thereof, the present invention is not so limited. Prosthesis 10", as well as prosthesis 10, 10', includes at least two different textile portions in various proportions and shapes.

Figure 7:
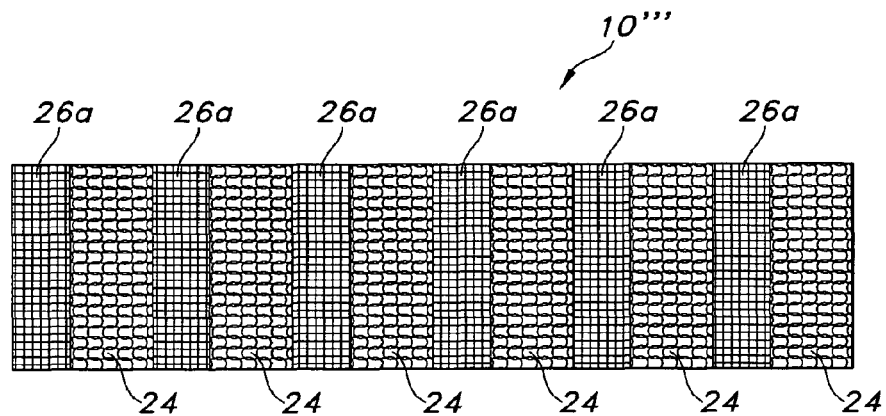
FIG. 7 is a side longitudinal view of yet another embodiment of the prosthesis of FIG. 1 taken along the A-A axis depicting a flared prosthesis with composite textile surface with multiple first and second textile portions.

Further, as depicted in FIG. 7, the composite textile prosthesis 10'" of the present invention may have a plurality of different textile portions. Prosthesis 10'" may have alternating first textile portions 24 and second textile portions 26a along the longitudinal length of the prosthesis. Such a varied textile pattern is useful where, but not limited to, body lumens that are curved or where there is a need to vary the textile properties, such as compliance, dilation resistance or stretchability, along the length of prosthesis 10'".

Figure 8:
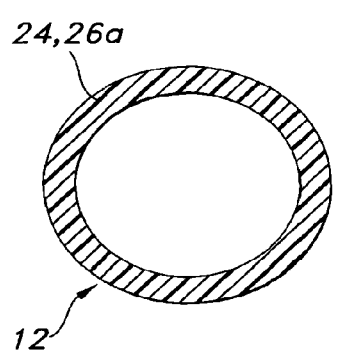
FIG. 8 is a cross sectional view of the prosthesis of FIG. 4 taken along the B-B axis depicting a textile tubular wall.
Figure 9:
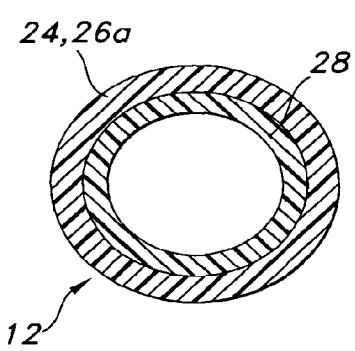
FIG. 9 is a cross sectional view of the prosthesis of FIG. 4 taken along the B-B axis depicting a tubular wall having a textile outer wall portion and a polymeric inner layer wall portion.
Figure 10:
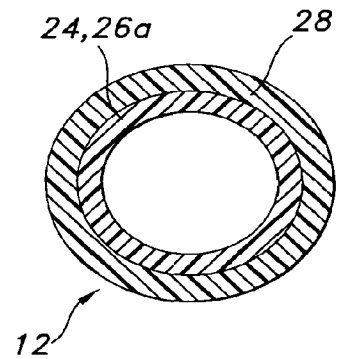
FIG. 10 is a cross sectional view of the prosthesis of FIG. 4 taken along the B-B axis depicting a tubular wall having a textile inner wall portion and a polymeric outer layer wall portion.
Figure 11:
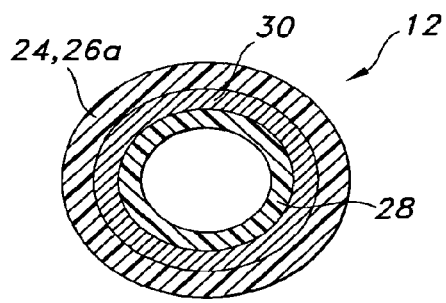
FIG. 11 is a cross sectional view of the prosthesis of FIG. 4 taken along the B-B axis depicting a tubular wall having a textile outer wall portion, a polymeric inner layer wall portion, and a stent disposed therebetween.
Figure 12:
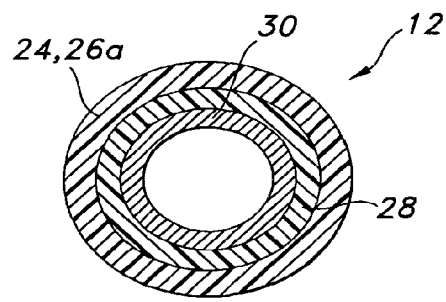
FIG. 12 is a cross sectional view of the prosthesis of FIG. 4 taken along the B-B axis depicting a tubular wall having a textile outer wall portion, a polymeric inner layer wall portion, and a stent disposed on the inner surface of the polymeric inner layer.
Figure 13:
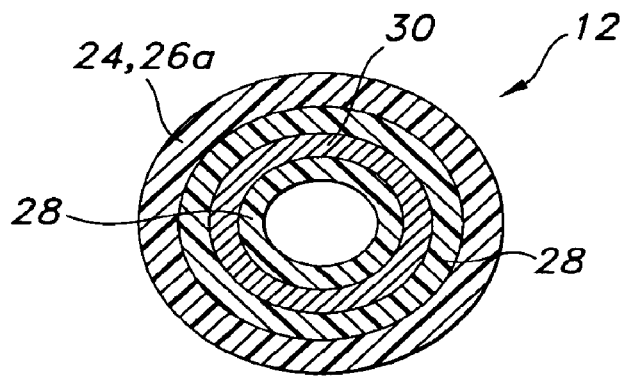
FIG. 13 is a cross sectional view of the prosthesis of FIG. 4 taken along the B-B axis depicting a tubular wall having a textile outer wall portion and a stent having interior and exterior polymeric wall portions.
Figure 14:
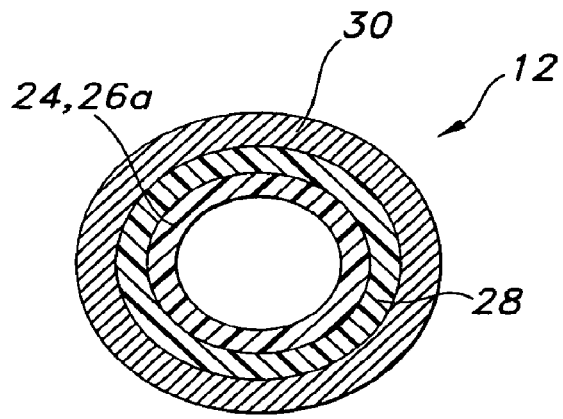
FIG. 14 is a cross-sectional view of the prosthesis of FIG. 4 taken along the B-B axis depicting a tubular wall having an exterior stent portion with a polymeric inner layer portion disposed on the inner surface of the stent and a textile inner wall portion disposed on the interior surface of the polymeric portion.
Figure 15:
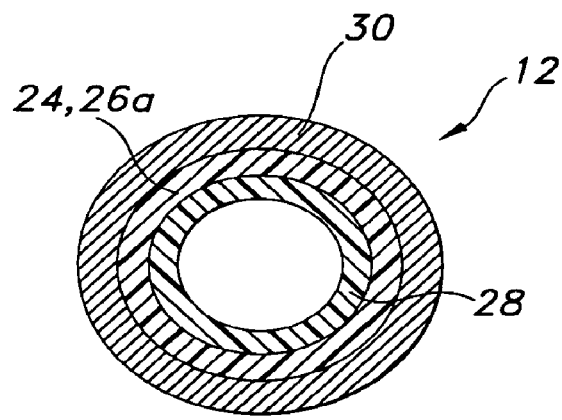
FIG. 15 is a cross-sectional view of the prosthesis of FIG. 4 taken along the B-B axis depicting a tubular wall having an exterior stent portion with a textile inner wall portion disposed on the inner surface of the stent and a polymeric inner layer portion disposed on the interior surface of the textile portion.
Figure 16:
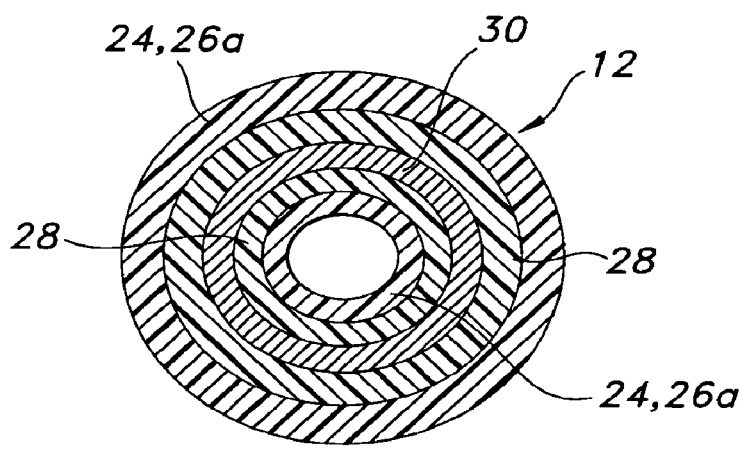
FIG. 16 is a cross-sectional view of the prosthesis of FIG. 4 taken along the B-B axis depicting a tubular wall having an exterior textile inner wall portion disposed over a first polymeric inner layer portion which is disposed on an outer surface of a stent with a second polymeric inner layer portion disposed on the inner surface of the stent and an interior textile portion disposed over the inner surface of the second polymeric layer.

FIGS. 8-16 depict cross-sectional views of the prosthesis 10 of FIG. 4 taken along the B-B or the B'-B' axes. As depicted in FIG. 8, the cylindrical wall 12 of prosthesis 10 is a textile layer, i.e., either first textile portion 24 or second textile portion 26a. As depicted in FIG. 9, the cylindrical wall 12 may further include a polymeric layer or tube 28 circumferentially disposed about the inner surface of first textile portion 24, second textile portion 26a, or both first and second textile portions 24, 26a. As depicted in FIG. 10, the polymeric layer or tube 28 may be circumferentially disposed about the exterior of the first textile portion 24, the second textile portion 26a or both the first and second textile portions 24, 26a. Further, as depicted in FIG. 11, the cylindrical wall 12 may consist of the outer textile portions 24, 26a and a stent 30 circumferentially disposed about the inner surface of the textile portions to define a stent-graft 32. The stent-graft 32 may optionally include the polymeric layer or tube 28 circumferentially disposed about the interior portions of stent 30, as depicted in FIG. 11, or circumferentially disposed about exterior portions of stent 30, as depicted in FIG. 12, or circumferentially disposed about both interior and exterior portions of stent 30, as depicted in FIG. 13. Alternatively, the polymeric layer or tube 28 may be directly associated with stent 30 to provide a unitary polymeric covered stent (not shown). Further, stent-graft 32 may be formed as having textile and/or polymeric portions disposed to interior portions of stent 30. As depicted in FIG. 14, stent-graft 32 may include stent 30 having the polymeric tube or layer circumferentially disposed about the interior portions of the stent 30 with textile portions 24, 26a being circumferentially disposed about the interior portions of the polymeric tube or layer 28. As depicted in FIG. 15, stent-graft 32 may alternatively include stent 30 having the textile portions 24, 26a circumferentially disposed about the interior portions of the stent 30 with polymeric tube or layer 28 being circumferentially disposed about the interior portions of the textile portions 24, 26a. As depicted in FIG. 16, stent-graft 32 may alternatively include stent 30 having polymeric tubes or layers 28 circumferentially disposed over the interior and exterior stent surfaces with the textile portions 24, 26a being circumferentially disposed about the polymeric tubes or layers 28 to provide a stent graft 32 having both interior and exterior textile surfaces.

Figure 17:
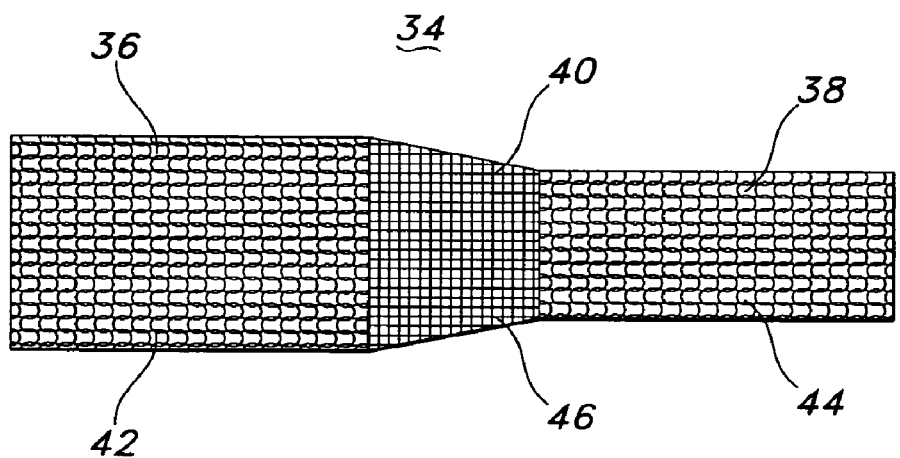
FIG. 17 is side longitudinal view of a shaped prosthesis of the present invention having a composite textile surface.

The present invention, however, is not limited to substantially uniform single lumen implantable devices, such as the above-described prosthesis 10 and stent-graft 32. As depicted in FIG. 17, shaped prosthesis 34 consists of straight portions 36, 38 of different diameters interconnected by a transitional portion 40. Although transitional portion 40 is shown as an inwardly tapered shape in FIG. 17, other shapes may suitably be used. The different portions 36, 38, 40 of shaped prosthesis 30 are different textile portions 42, 44, 46. Desirably, textile portions 42 and 44, which can be the same or different, are high stretch or high permeability textile portions as compared to textile portion 46. Preferably, textile portion 46 is a woven portion and textile portions 42, 44 are knitted portions. When shaped prosthesis 34 is a stent-graft, such as any of the above-described stent-grafts 32, a woven textile portion 46 exhibits less dilation as compared to textile portions 42, 44. Dilation effects are more pronounced at areas of dimensional change, especially when going from a large diameter artery to a smaller diameter artery, and a woven pattern at textile portion 40 prohibits dilation as compared to typical knitted patterns.

Figure 18:
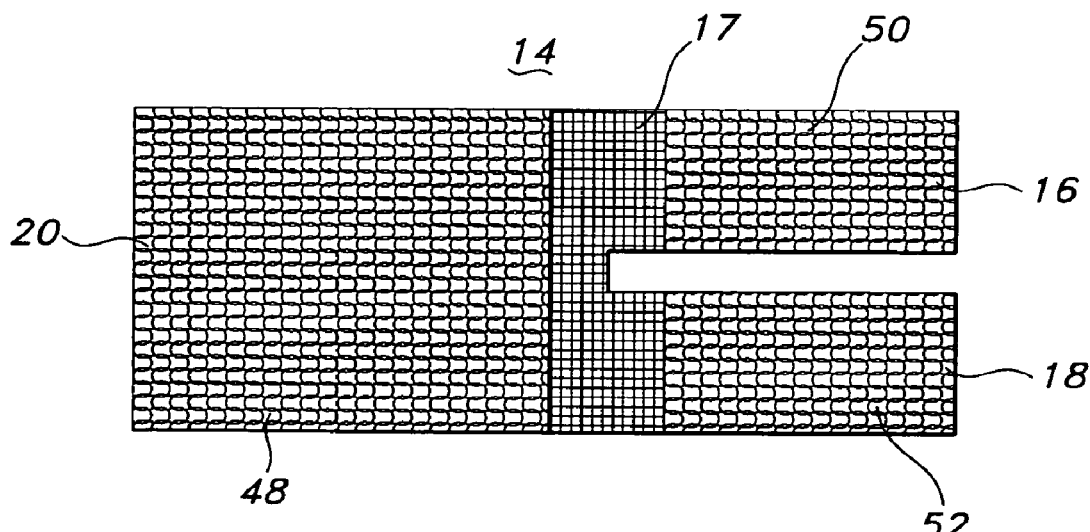
FIG. 18 is side longitudinal view of a bifurcated prosthesis of the present invention having a composite textile surface with the legs and body being a first textile portion and having a second textile portion disposed therebetween.
Figure 19:
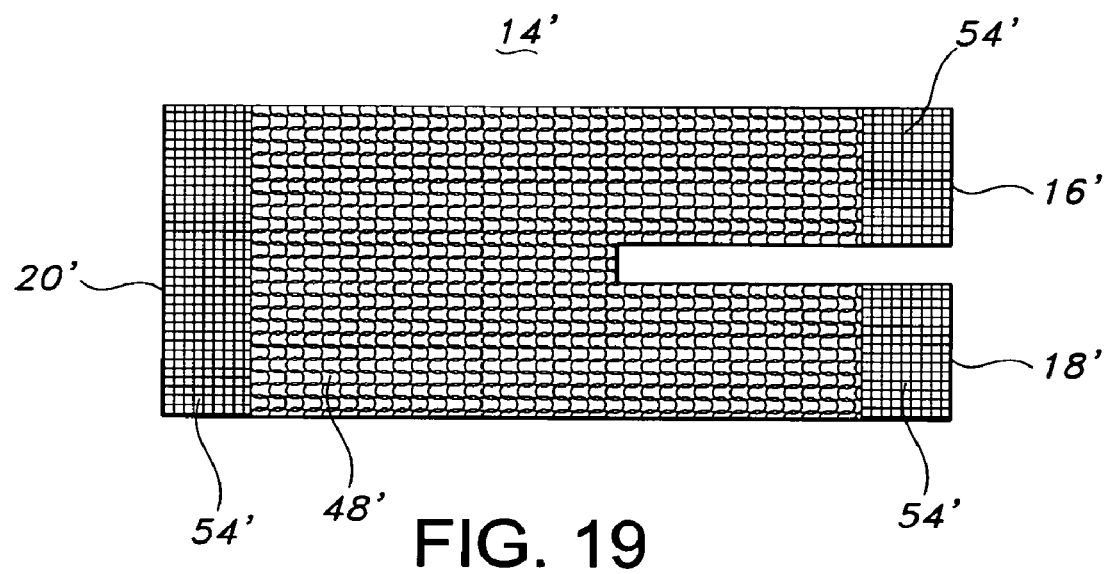
FIG. 19 is side longitudinal view of another bifurcated prosthesis of the present invention having a composite textile surface with the legs and body being a first textile portion and having a second textile portion at the terminal ends thereof.
Figure 20:
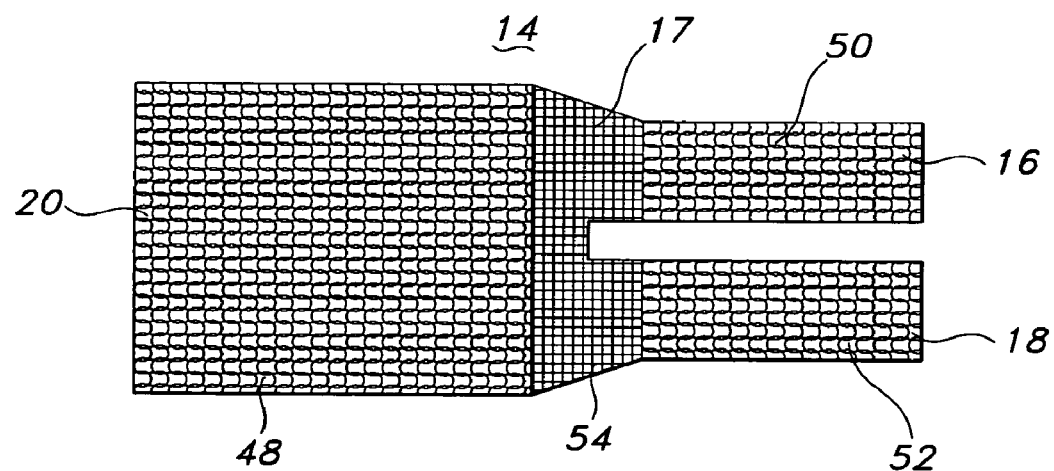
FIG. 20 is side longitudinal view of yet another bifurcated prosthesis of the present invention having a composite textile surface with the legs and body being a first textile portion and having a second flared textile portion disposed therebetween.
Figure 21:
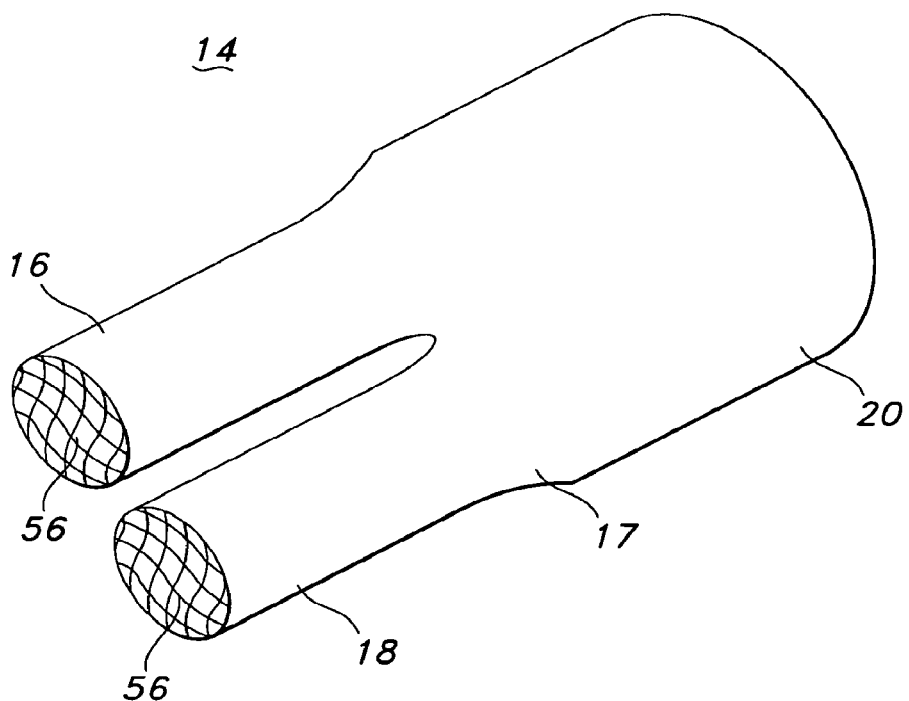
FIG. 21 is perspective view of a bifurcated stent/graft of the present invention.
Figure 22:
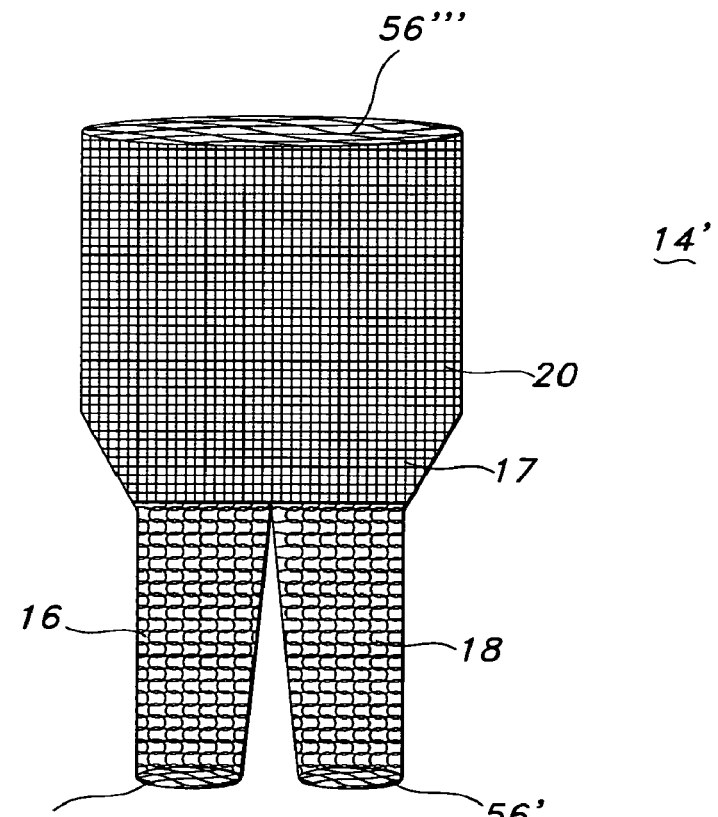
FIG. 22 is a perspective view of another embodiment of a bifurcated stent-graft of the present invention.

FIG. 18 is a top surface view of the bifurcated prosthesis 14 of FIG. 2. As depicted in FIG. 18, legs 16, 18 and main body 20 are connected via a transitional portion 17. The transitional portion 17 is often referred to as a crotch area of a bifurcated prosthesis. The transitional portion 17 may be a substantially straight walled portion or may be shaped or tapered as shown in FIG. 20. The transitional portion 17 is often subject to increased pressure variations as compared to the main body 20 and the legs 16, 18. Accordingly, transitional area 17 of the present invention has a textile portion 54 of lower permeability and/or lower longitudinal stretchability as compared to the textile portions 48, 50, 52 of the main body 20 and legs 16, 18, respectively. Textile patterns with lower textile permeability and/or longitudinal stretchability often have lower radial dilation tendencies as compared to textiles of higher permeability and/or higher longitudinal stretchability. Desirably, textile portion 54 is a woven patterns and textile portions 48, 50, 52, which can be the same or different, are knitted patterns. Such textile patterns are especially useful when bifurcated prosthesis 14 is a bifurcated stent-graft as depicted in FIG. 22 where stent 56 is internally disposed along the cylindrical walls of textile portions 16, 18, 17, 20. Further, as depicted in FIG. 19, bifurcated prosthesis 14' may include a textile composite where the main body 20' and the legs 16', 18' are of one textile portion 48', but where the terminal portions of the main body 20' and the legs 16', 18' are of another textile portion 48'. Desirably, textile portion 54' is a woven patterns and textile portion 48' is a knitted patterns.

Stent 30 or stent 56 may be attached to adjoining textile portions through mechanical securement or bonding. Mechanical securement includes, but is not limited to, the use of sutures, anchoring barbs, textile cuffs, and the like. Bonding includes, but is not limited to, chemical bonding, for instance adhesive bonding, thermal bonding or welding, ultrasonic bonding or welding, and the like. The use of sutures and these bonding techniques may also be suitably used to secure different textile portions to one and the other, such as textile portions 26a and 26b being secured to textile portion 24, textile portions 42 and 44 being secured to textile portion 46, textile portions 48, 50 and 52 being secured to textile portion 50, and the like.

Various stent types and stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

Figure 23:
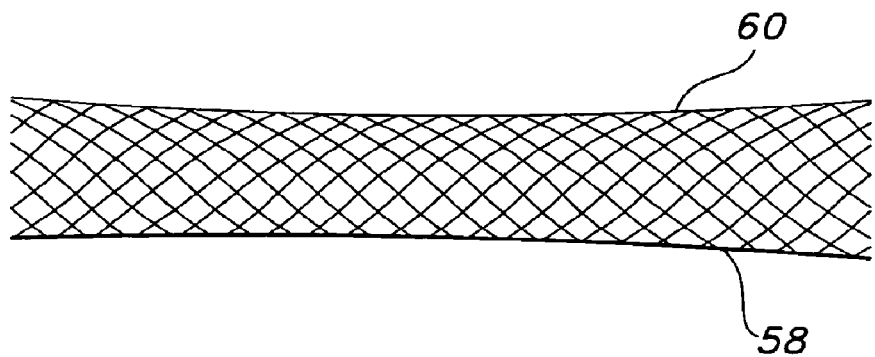
FIG. 23 is a longitudinal view of a wire stent of the present invention.

The configuration of stent 30 or bifurcated stent 56 may be of any suitable geometry. As shown in FIG. 23, wire stent 58 is a hollow tubular structure formed from wire strand 60 or multiple wire strands. Wire stent 58 may be formed by, for example, braiding or spinning wire strand(s) 60 over a mandrel (not shown). Wire stent 58 is capable of being radially compressed and longitudinally extended for implantation into a bodily lumen. The degree of elongation depends upon the structure and materials of the wire stent 58 and can be quite varied, for example, about 5% to about 200% of the length of wire stent 58. The diameter of wire stent 58 may also become several times smaller as it elongates. Desirably, stents that have substantial dimensional variations, such as bifurcated stent 56 or a stent associated with the shaped prosthesis 34, are wire stents. Unitary stent structures may be obtained by braiding and/or filament winding stent wires to obtain complex stent geometries, including complex stent geometries, including complex bifurcated stents. Alternatively, stent components of different sizes and/or geometries may be mechanically secured by welding or suturing. Additional details of wire stents of complex geometry are described in U.S. Pat. Nos. 6,325,822 and 6,585,758, the contents of which are incorporated herein by reference.

Figure 24:
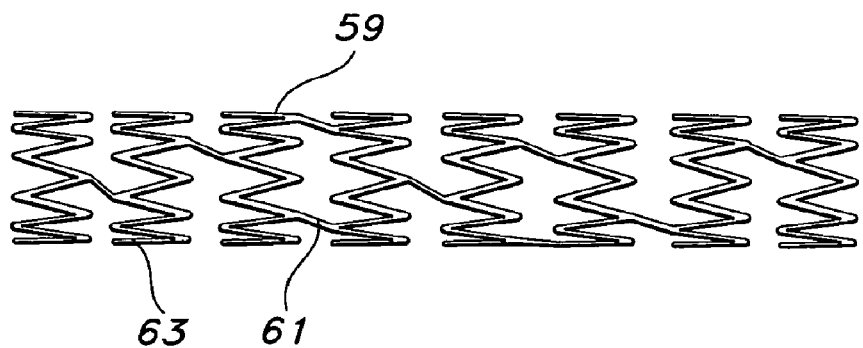
FIG. 24 is a longitudinal view of a zig-zag stent of the present invention.

A zig-zag wire stent 59 is also useful as stent 30 or bifurcated stent 56. Wire strand 63 is being arranged in what can be described as a multiple of "Z" or "zig-zag" patterns to form a hollow tubular stent. The different zig-zag patterns may optionally be connected by connecting member 61. Further, zig-zag wire stent 59 is not limited to a series of concentric loops as depicted in FIG. 24, but may be suitably formed by helically winding of the "zig-zag" pattern over a mandrel (not shown).

Figure 25:
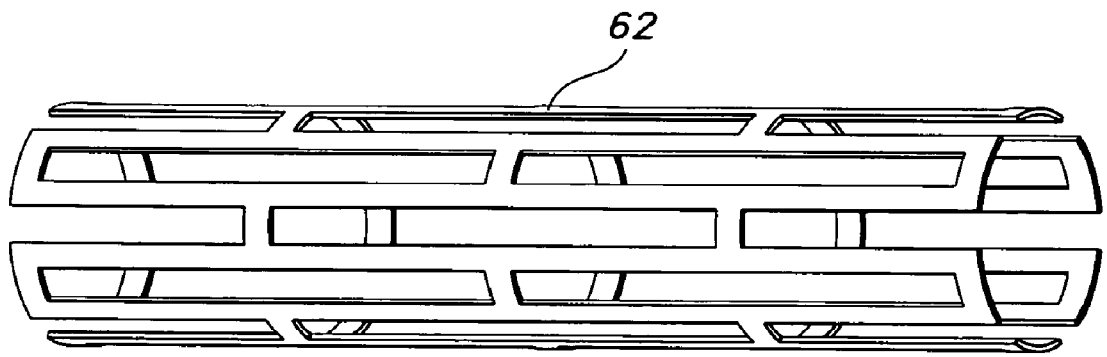
FIG. 25 is a perspective view of slotted stent of the present invention.

A slotted stent 62 is also useful as part of the stent-graft 32. As depicted in FIG. 25, slotted stent 62 is suitably configured for implantation into a bodily lumen (not shown). Upon locating the slotted stent 62 at the desired bodily site, slotted stent 62 is radially expanded and longitudinally contracted for securement at the desired site.

Figure 26:
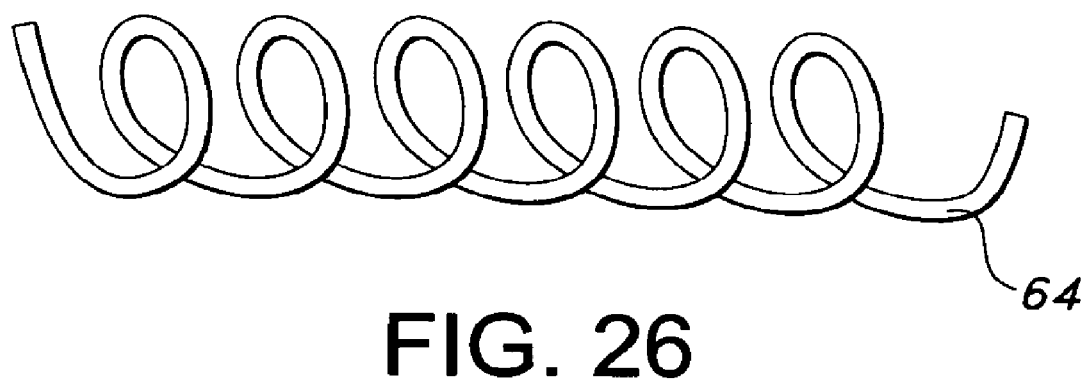
FIG. 26 is a perspective view of a helical coil stent formed of a single wound wire according to the present invention.
Figure 27:
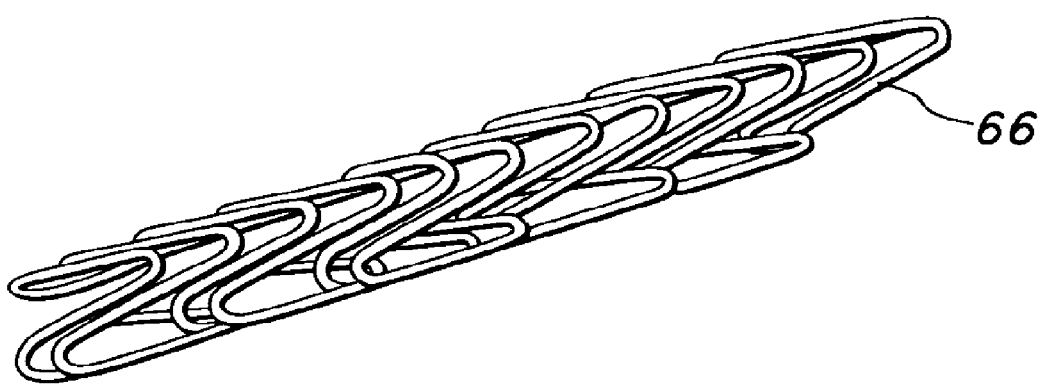
FIG. 27 is a perspective view of a stent having an elongate pre-helically coiled configuration according to the present invention.
Figure 28:
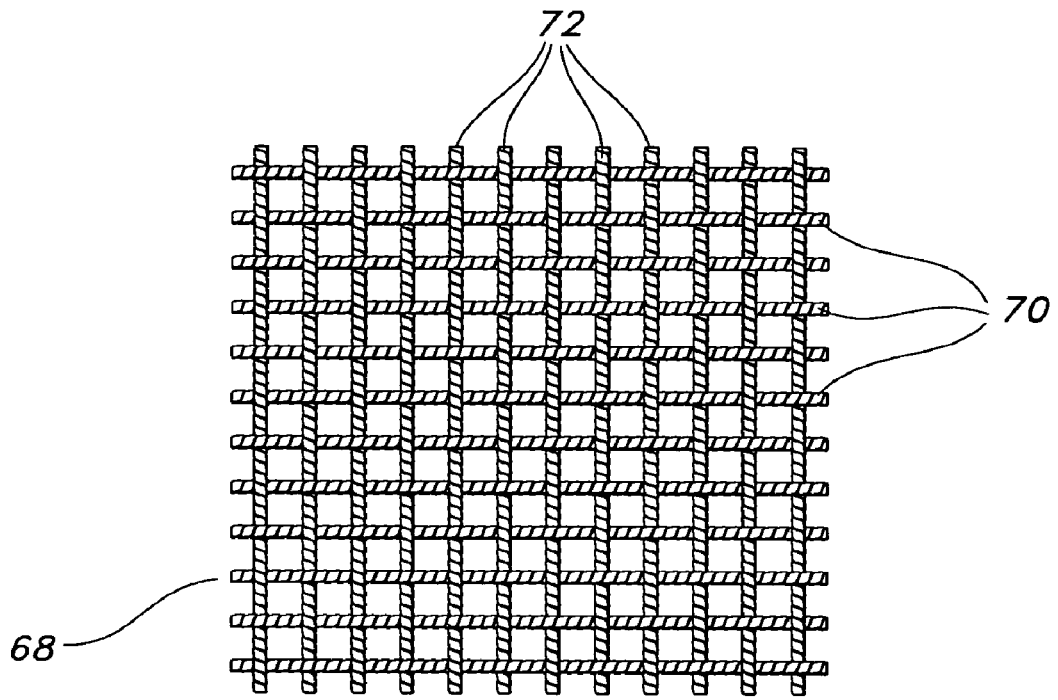
FIG. 28 is an expanded view of a woven portion of the textile prosthesis of the present invention.

Other useful stents capable of radial expansion are depicted in FIGS. 26 and 27. As depicted in FIG. 26, stent 64 is a helical coil which is capable of achieving a radially expanded state (not shown). Stent 66, as depicted in FIG. 27, has an elongate pre-helically coiled configuration as shown by the waves of non-overlapping undulating windings. These helically coiled or pre-helically stents, commonly referred to as nested stents, are also useful with the practice of the present invention.

Stent-graft composite devices are also contemplated having self-expanding stents and balloon expandable stents. Self-expanding stents include those that have a spring-like action which causes the stent to radially distend, i.e., expand and/or contract, or stents which expand due to the memory properties of the stent material for a particular configuration at a certain temperature. Balloon expandable stents require an applied force, typically from an expandable balloon on a catheter, to radially distend.

The stent-grafts of the present invention are not limited to the use of a single stent. For example, as depicted in FIG. 22, bifurcated prosthesis 14' may include may include stents 56' and 56", which may be the same or different, within the legs 16, 18 and include a stent 56" within the main body 20, where stent 56" is different from stents 56, 56'. For example, stent 56, 56' may be a self-expanding braided stent, and stent 56" may be a balloon-expandable sent, such as a slotted stent. Further, the textile portions of legs 16, 18 are advantageously knitted portions, and the textile portions of main body 20 are advantageously woven portions. Such features provide a bifurcated prosthesis 14' with enhanced compliance at legs 16, 18 and improved resistance to dilation at main body 20.

One type of polymeric or non-textile material particularly useful is polytetrafluoroethylene (PTFE). PTFE exhibits superior biocompatibility and low thrombogenicity, which makes it particularly useful as vascular graft material in the repair or replacement of blood vessels. Desirably the non-textile layer is a tubular structure manufactured from expanded polytetrafluoroethylene (ePTFE). The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to 600 percent by linear dimension. The physically modified ePTFE tubular structure is able to be elongated or expanded and then returned to its original state without an elastic force existing therewithin. Such a physically modified ePTFE tubular structure is advantageously used in conjunction the devices of the present invention.

One example of a physically modified ePTFE tubular structure is one that has circumferentially oriented nodes and longitudinally traversing fibrils, where the fibrils have been hingeably rotated to provide for the enhance expansion properties. Additional details of the physically modified ePTFE and methods for making the same can be found in commonly assigned application titled, "ePTFE Graft With Axial Elongation Properties", assigned U.S. application Ser. No. 09/898, 415, filed on Jul. 3, 2001, published on Jan. 9, 2003 as U.S. Application Publication No. 2003/0009210 A1, the contents of which are incorporated by reference herein.

The textile portions of the present invention can have virtually any textile construction, including weaves, knits, braids, filament windings and the like. Desirably, textile portions 26a, 26b, 46 and 54 are woven textile portions. Useful weave patterns include simple weaves, basket weaves, twill weaves, satin weaves, velour weaves and the like. The weave pattern 68 for these woven portions includes warp yarns 70 running along the longitudinal length (as indicated by vector L in FIG. 1) of the woven product and fill yarns 72 running around the circumference (as indicated by vector C in FIG. 1) of the product the warp, the fill yarns being at approximately 90 degrees to one another with fabric flowing from the machine in the warp direction.

Desirably, textile portions 24, 42, 44, 48, 50, and 52 are knitted textile portions. Knitting involves the interlooping or stitching of yarn into vertical columns (wales) and horizontal rows (courses) of loops to form the knitted fabric structure.

Figure 29:
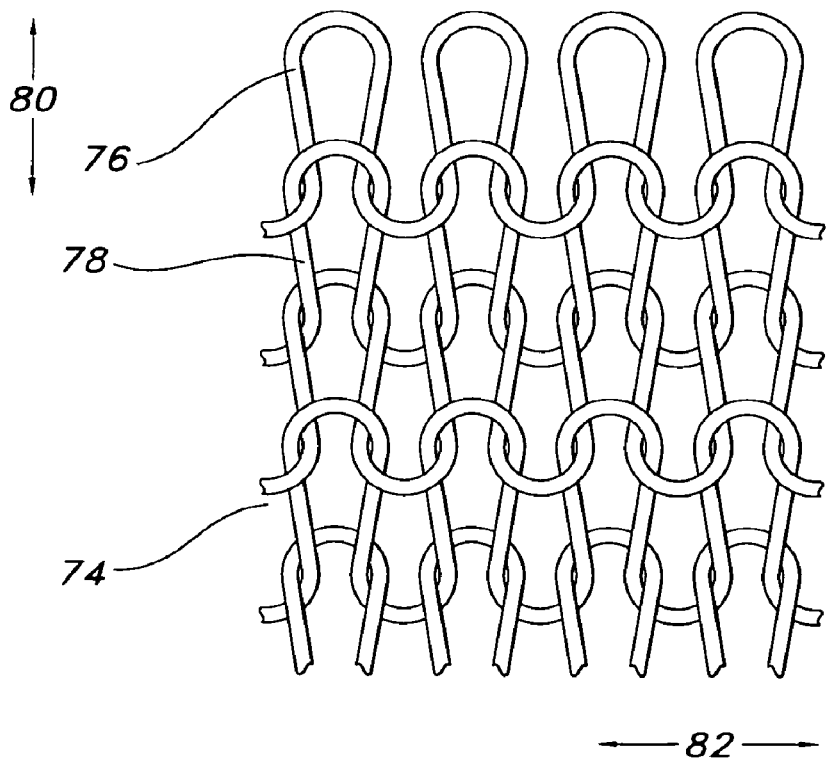
FIG. 29 is an expanded view of a knitted portion of the textile prosthesis of the present invention.

Warp knitting is particularly useful with the knitted textile portions of the present invention. In warp knitting, the loops are formed along the textile length, i.e., in the wale or warp direction of the textile. As depicted in FIG. 29, for a tubular textile, such as prosthesis 10, stitches in the axial or longitudinal direction (L) of the tubular textile are called wales (indicated by vector 80 in FIG. 29) and stitches in the radial or circumferential direction (C) of the tubular textile are called courses (indicated by vector 82 in FIG. 29). Yarns 76 and 78 interloop in the warp direction to form a warp-knitted 74.

Knitting patterns useful with the present invention include conventional warp-knitted patterns and high-stretch, warp-knitted patterns. Commonly used warp-knitted patterns include locknit (also referred to as tricot or jersey knits), reverse locknit, sharkskin, queenscord and velour knits. Useful high stretch, warp-knitted patters include those with multiple patterns of diagonally shifting yarns, such as certain modified atlas knits which are described in U.S. Pat. No. 6,540,773, the contents of which are in incorporated herein by reference. Other useful high-stretch, warp knitted patterns include certain patterns with multiple needle underlap and one needle overlap, such as those patterns described in U.S. Pat. No. 6,554,855 and U.S. Patent Application Publication No. 2003/0204241 A1, the contents of which are incorporated herein by reference.

Figure 30:
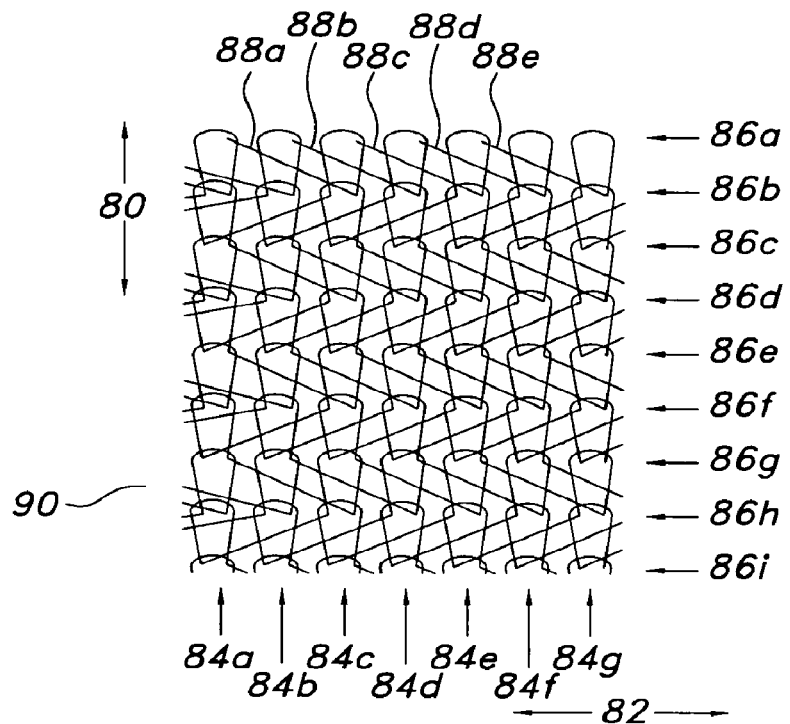
FIG. 30 is an expanded view of a knitted portion having a two-needle underlap of the textile prosthesis of the present invention.

FIG. 30 is an illustration of a high-stretch knitted pattern 90 useful with the present invention having a two needle underlap. In FIG. 30, needle positions in the course direction, i.e., vector 82, are noted by element numbers 84a through 84g and needle positions in the wale direction, i.e., vector 80, are noted by element numbers 86a through 86i. Yarn 88a travels in the course direction from needle position 84a to needle position 84c, or two needle positions, before interlooping with yarn 88c. Yarn 88a then travels two needle positions in the opposite course direction to interloop with a yarn. This alternating two needle position movement is repeated with different yarns to form the knitted pattern 90 with a two needle underlap.

Figure 31:
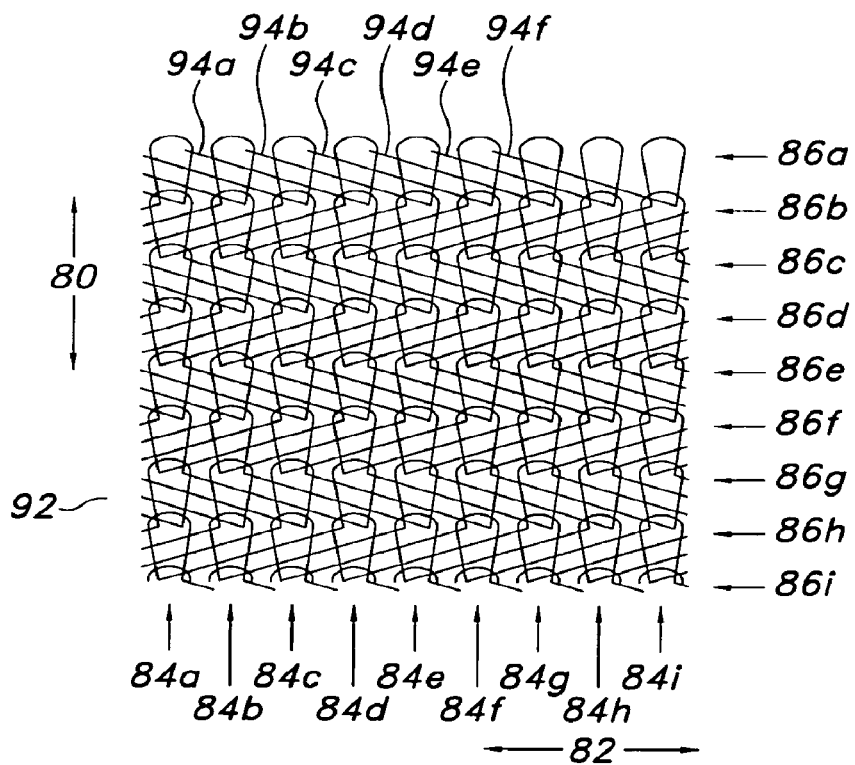
FIG. 31 is an expanded view of a knitted portion having a three-needle underlap of the textile prosthesis of the present invention.

The knitted portion 92, as illustrated in FIG. 31, is characterized as a three-needle underlap. In FIG. 31, needle positions in the course direction, i.e., vector 82, are noted by element numbers 84a through 84i and needle positions in the wale direction, i.e., vector 80, are noted by element numbers 86a through 86i. Yarn 94a travels in the course direction from needle position 84a to needle position 84d, or three needle positions, before interlooping with yard 94d. Yarn 94a then travels three needle positions in the opposite course direction to interloop with a yarn. This alternating three needle position movement is repeated with different yarns to form the knitted pattern 92 with a three needle underlap.

The knitted patterns 74, 90 and 92 are depicted as a single knitted layer in FIGS. 29-31. The textile portions of the present invention, however, are not so limited. For instance, the knitted portions may also include more than one layer of interconnected yarns. In such a multi-layered knitted textile, yarns from one layer are often interlooped with yarns in another layer to form the multi-layered knitted textile.

The different textile portions of the present invention are desirably securably attached to one and the other. For example, one textile portion 24, 42, 44, 48, 50, and 52 is desirably securably attached to another textile portion 26a, 26b, 46, and 54. As depicted in FIGS. 32-41, an attachment means is useful for securing one textile portion 98, such as a knitted textile portion, to another textile portion 100, such as a woven portion. Useful, but non-limiting, attachment means includes mechanical means, such as clips, sutures or other engageable yarns, adhesive means, or fuseable means.

Figure 32:
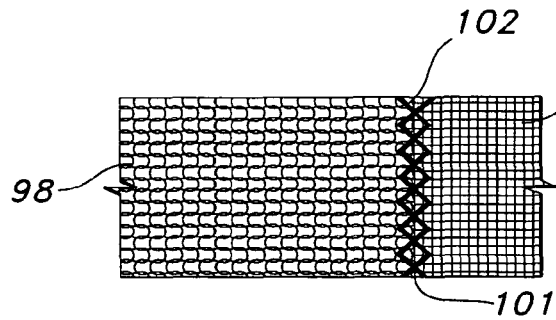
FIG. 32 is a depiction of two different textile portions of the present invention being securably attached to one and the other by sutures.

As depicted in FIG. 32, sutures 102 may be used to mechanically secure the engaging portions 101 of the textile portions 98 and 100 to one and the other. Sutures 102 may be made from synthetic materials such as synthetic polymers, including, but not limited to, polyesters, including PET polyesters, polypropylenes, polyethylenes, polyurethanes and polytetrafluoroethylenes.

Figure 33:
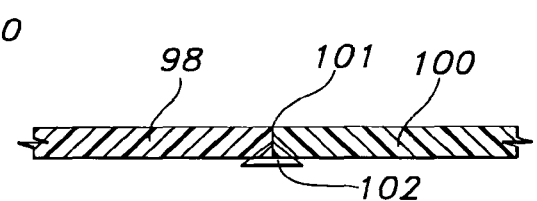
FIG. 33 is a cross-sectional view of the sutured textile portions of FIG. 32 depicting the textile portions being sutured in an end-to-end arrangement.

As depicted in FIG. 33, textile portions 98 and 100 may be secured to one and the other in an end-to-end arrangement with sutures 102 where the sutures 102 are exposed on only one side of the textile wall. In other words, one side of the textile wall at the engaging portions 101 has exposed threads or sutures while the other side of the textile wall does not have exposed sutures thereby providing for a seamless textile transition at that wall surface.

Figure 34:
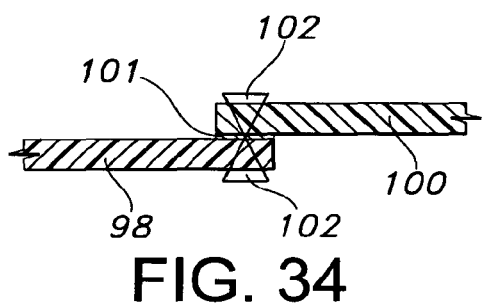
FIG. 34 is a cross-sectional view of the sutured textile portions of FIG. 32 depicting the textile portions being sutured in a top-to-bottom arrangement.

The present invention, however, is not limited to the suturing of different textile portions in an end-to-end arrangement. As depicted in FIG. 34, textile portions 98 and 100 may be secured to one and the other in a top-to-bottom arrangement with sutures 102. Desirably sutures 102 traverse both textile portions 98 and 100.

Figure 35:
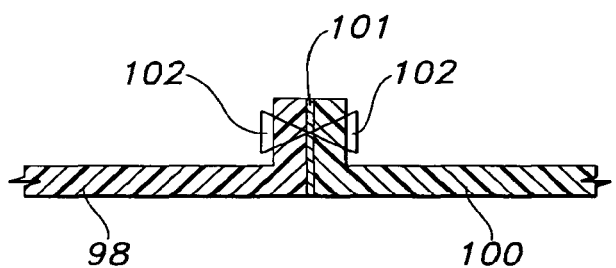
FIG. 35 is a cross-sectional view of the sutured textile portions of FIG. 32 depicting the textile portions being flipped and sutured in a top-to-bottom arrangement.
Figure 36:
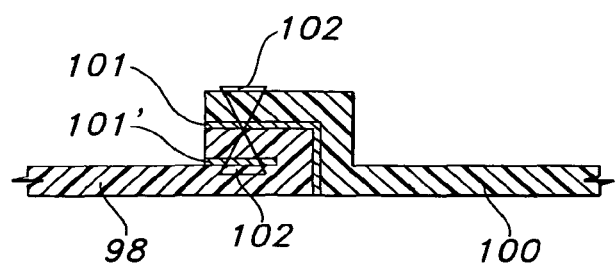
FIG. 36 is a cross-sectional view of the sutured textile portions of FIG. 35 depicting the sutured portions being laid flat against a textile wall.

Moreover, as depicted in FIG. 35, the ends of the textile portions 98 and 100 may be folded upward or away from the major longitudinal extend of the textile portions 98 and 100. Sutures 102 may then be suitably used to secure the engaging portions 101. Additionally, as depicted in FIG. 36 the sutured engaging portions may be folded back toward textile portion 98 or 100, such that the sutured portions or sutured flap any engage one of the textile portions 98 and 100 at engaging location 101'. The sutured textile portion 98 or 100 may then be secured to the engaging textile portion 98 or 100 portion at engaging location 101'. Securement may include additional sutures (not shown) or use of an adhesive or heat bonding, as described below.

Figure 37:
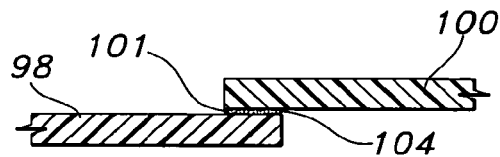
FIG. 37 is a depiction of two different textile portions of the present invention being securably attached to one and the other in a top-to-bottom fashion by an adhesive.
Figure 38:
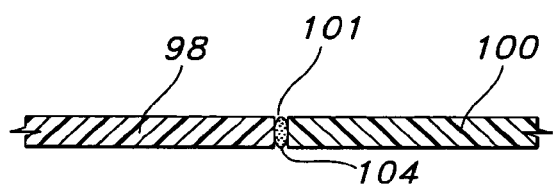
FIG. 38 is a depiction of two different textile portions of the present invention being securably attached tone and the other in a side-to-side fashion by an adhesive.

As depicted in FIGS. 37 and 38, textile portion 98 may be securably attached to textile portion 100 in a top-to-bottom fashion or in a side-to-side fashion by means of an adhesive 104. Nonlimiting examples of useful material for the adhesive 104 include various biocompatible, elastomeric bonding agents such as urethanes, styrene/isobutylene/styrene block copolymers (SIBS), silicones, and combinations thereof.

Figure 39:
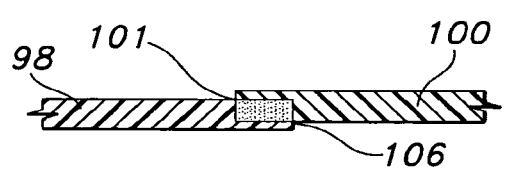
FIG. 39 is a depiction of two different textile portions of the present invention being securably attached to one and the other in a top-to-bottom fashion by fusingly bonding portions thereof.
Figure 40:
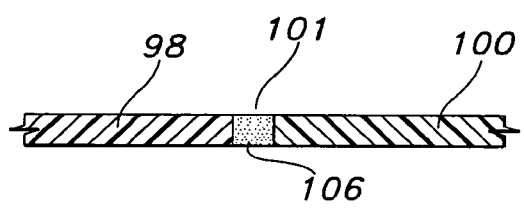
FIG. 40 is a depiction of two different textile portions of the present invention being securably attached to one and the other in a side-to-side fashion by fusingly bonding portions thereof.

As depicted in FIGS. 39 and 40, textile portion 98 may be securably attached to textile portion 100 in a top-to-bottom fashion or in a side-to-side fashion by means of a fusing means 106. Fusing means 106 includes, but is not limited to, the application of heat, radiation or localized energy to melt engaging portions 101 of the textiles 98 and 100 or to melt a resin material contained thereat. For example, localized energy may be supplied to fusingly engage polyester yarns which have a melting point of about 260° C. Alternatively, a lower melting resin, resin-containing yarn, or a lower melting yarn may be used at the engaging portions 101 of the textile portions 98 and 100. For example, certain polyethylenes, copolyethylenes, copolyolefins, polyurethanes and copolyesters, as disclosed in U.S. Pat. No. 5,178,630, the contents of which is incorporated herein by reference, may be selected that have a melting point from about 110° C. to about 220° C. may suitably be used as the fusing means 106 for the textile portions 98 and 100.

Figure 41:
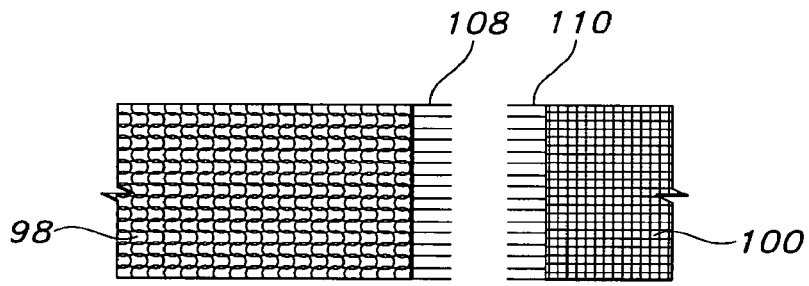
FIG. 41 is a depiction of two different textile portions of the present invention having extending yarns which are used to securably attach or form the different textile portions of the prosthesis of FIG. 4 taken along the B-B axis depicting

As depicted in FIG. 41, textile portion 98 may be securably attached to textile portion 100 by means of engageable yarns 108 and 110. Yarns 108 and 110 are trailing yarns, such as yarns that are not interlaced or interlooped in their textile pattern, from the respective textile patterns in textile portions 98 and 100. The yarns 108 and 110 may be tied or hemmed together (not shown) to securably attach the textile portions 98 and 100 to one and the other. The yarns 108 and 110 may also be integrated into the different textile portions 98 and 100 to form a unitary textile connection (not shown). For example, after textile portion 98 is formed, spools (not shown) containing the yarns 108 may be transferred from the textile machine, such as a knitting machine (not shown), used to form the textile portion 98 to a different textile machine, such as a weaving machine (not shown) used to form textile portion 100. The two textile portions 98 and 100 may then be interlaced or interloped by incorporation of yarns 108 or 110 into the different textile processing machines by transferring spools containing these yarns.

The prostheses of the present invention may be coated with a bio-absorbable coating, such as collagen, albumin, elastin and the like. Such coatings are known in the art and are desirable in vascular and endovascular graft applications to seal the graft and thereby prevent blood loss in the early stages of implantation. Other coatings which may be used include those disclosed in U.S. Pat. No. 5,851,229, which is incorporated herein. The '229 patent discloses a sealant composition that includes at least two polysaccharides in combination to form a hydrogel or solgel. Sealant compositions may include a bioactive agent and or be cross-linked subsequent to the application of these compositions to the substrate surface. Additionally, U.S. Pat. No. 5,209,776, incorporated herein, discloses a composition that includes a first protein component that is preferably collagen and a second protein-supporting component that can be a proteoglycan, a saccharide or a polyalcohol.

Axial yarns are added in some cases to limit a textile structure from stretching beyond a desired amount, and thereby significantly reducing the potential for scissoring action of the yarns. This scissoring or shearing action is detrimental to the body's healing process. The scissoring action of the strands tends to prevent the tissue and blood vessels from infiltrating the pores of the structure. Additionally, an axial yarn may be dyed and inserted into the textile structure subsequent to or during the braiding process. A dyed axial yarn positioned in the outer surface of the prosthesis aids the surgeon during implantation to indicate whether the prosthesis is straight and not twisted during the procedure.

The prosthesis may include a radiopaque guideline or marker to provide means for viewing the implanted prosthesis fluoroscopically. The marker may extend the length of the prosthesis. Other patterns for markers may also be employed. Radiopaque markers assist the surgeon to visualize the prosthesis both during and after implantation. The marker helps show the surgeon that the prosthesis is properly positioned. Also, it will indicate whether the prosthesis has dilated or collapsed after implantation.

The knitted textile graft of the present invention is desirably made on a warp-knitting machine (not shown) using a double needle bar. A useful number of needles per inch for warp knitting is from about 18 to about 36. About 28 to 30 needles per inch are particularly suitable. The trellis of the graft is usually made from a yarn having count from 30 to 300 denier. Desirably, the range of yarn counts for the trellis is from about 30 to about 80. A particularly suitable yarn count is about 40 denier. Moreover, the trellis yarn may be a single ply, a double ply or a multi-ply. The term "multi-ply" is used herein to indicate more than two-ply.

In one aspect of the present invention, the knitted textile graft is a knit structure of a single layer with at least a two-needle underlap. Because of the single layer construction the textile wall thickness is minimized to yield a low profile knitted textile graft. The textile wall thickness is from about 0.2 to about 0.4 millimeters. Desirably, the textile wall thickness is from about 0.27 to about 0.31 millimeters. Furthermore, the knitted textile graft of the present invention has a burst strength from about 11 kg/cm$^2$ to about 16 kg/cm$^2$ (about 150 psi to about 220 psi). Desirably, the knitted textile graft of the present invention has a burst strength from about 13 kg/cm$^2$ to about 14 kg/cm$^2$ (about 170 psi to about 190 psi). The stretchability of the knitted textile graft is desirably 5 to 220 percent at a one-kilogram of load. Knitted textile grafts with a stretchability of about 50 to 220 percent at one-kilogram load are also useful. Knitted textile grafts with a stretchability of about 90 to 200 percent at one-kilogram load are also useful. Furthermore, knitted textile grafts with a stretchability of about 120 to 160 percent at one-kilogram load are also useful.

Any type of textile product can be used as yarns for the knitted or woven portions of the present invention. Of particular usefulness in forming the fabric portions of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The yarns used in forming the textile grafts of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET).

After knitting or weaving the textile portion of the present invention, the textile prosthesis is optionally cleaned or scoured in a basic solution of warm water, e.g., about 50° C. to about 65° C. (about 120° F. to about 150° F.), and detergent. The textile is then rinsed to remove any remaining detergent.

After the textile prosthesis is optionally scoured, the prosthesis is compacted or shrunk to reduce and control, in part, the porosity of the graft. Porosity of a knitted material is measured on the Wesolowski scale and by the procedure of Wesolowski. In the Wesolowski test, a fabric test piece is clamped flatwise and subjected to a pressure head of about 120 mm. of mercury. Readings are obtained which express the number of millimeters of water permeating per minute through each square centimeter of fabric. A zero reading represents absolute water impermeability and a value of about 20,000 ml/min/cm$^2$ represent approximate free flow of fluid.

The porosity of the textile graft is often from about 30 ml/min/cm$^2$ to about 15,000 ml/min/cm$^2$ on the Wesolowski scale after being knitted on the double needle bar Raschel knitting machine. A more desirable porosity is from about 30 ml/min/cm$^2$ to about 5,000 ml/min/cm$^2$ on the Wesolowski scale and textile graft is compacted or shrunk in the wale direction to obtain the desired porosity. A solution of an organic component, such as hexafluoroisopropanol or trichloroacetic acid, and a halogenated aliphatic hydrocarbon, such as methylene chloride, is used to compact the textile graft by immersing it into the solution for up to 30 minutes at temperatures from about 15° C. to about 160° C. Other compacting solutions may suitably be used, such as those disclosed in U.S. Pat. Nos. 3,853,462 and 3,986,828, whose contents are incorporated by reference herein.

As noted above, preferably the tubular-knitted graft of the present invention is constructed of polyester which is capable of shrinking during a heat-set process. For instance, such grafts are typically flat-knitted in a tubular form. Due to the nature of the flat-knitting process, the tubular graft is generally flat in shape after knitting. Such grafts, however, when constructed of shrinkable polyester yarn, can be heat set on a mandrel to form a generally circular shape.

Such a heat-setting process is accomplished by first knitting the graft in a seamless tubular form out of a material capable of shrinking during a heat-setting or similar process. The graft may be preshrunk before it is placed on a mandrel. Preshrinking may be achieved by submitting the woven graft to moderate temperatures, such as from about 90° C. to about 205° C. (about 190° F. to about 400° F.). Usually the graft is placed in a medium for the preshrinking. Such a medium can include without limitation hot water, a chemical fluid, such as methylene chloride, or a gas, such as air or carbon dioxide. The graft of the present invention, however, may suitably be made without such a preshrinking of the yarns.

After the graft is knitted or alternatively knitted and preshrunk, the graft is placed on a mandrel, and heated in an oven at a temperature and time capable of causing the yarns of the graft to heat set to the shape and diameter of the mandrel. Preferably polyester yarns are used, and the heat setting is accomplished at time and temperatures appropriate for the material. For example, heat setting can be accomplished at about 90° C. to about 225° C. (about 190° F. to about 437° F.) for a period of about less than an hour. Temperatures in the range of about 130° C. to about 220° C. (about 260° F. to about 428° F.) are also useful. Desirably, temperatures from about 150° C. to about 215° C. (about 300° F. to about 419° F.) are also useful. Desirably, time periods from about 5 to about 30 minutes are useful. More desirably, with time periods from about 10 to about 20 minutes are useful. Other methods of heat setting known in the art may be employed. After such a heat setting process, the graft can be formed into a shape desired for implantation, having a generally circular inner lumen.

The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent.

The composite textile graft and non-textile layer, i.e., prosthesis 10, is desirably formed as follows. A thin non-textile, such as PTFE or ePFTE, tube is formed in a conventional forming process such as by tubular extrusion or by sheet extrusion where the sheet is formed into a tubular configuration. The non-textile tube is placed over a stainless steel mandrel (not shown) and the ends of the tube are secured. The non-textile tube is then spray coated with an adhesive solution, for example from about 1% to about 15% Corethane® urethane range, 2.5 W30 in DMAc. The coated non-textile tube is placed in an oven heated in a range from 18° C. to 150° C. for 5 minutes to overnight to dry off the solution. If desired, the spray coating and drying process can be repeated multiple times to add more adhesive to the non-textile tube. The coated non-textile tube is then covered with the textile graft to form a composite prosthesis. One or more layers of elastic tubing, preferably silicone, are then placed over this composite structure. This holds the composite structure together and assures that complete contact and adequate pressure is maintained for bonding purposes. The assembly of the composite graft within the elastic tubing is placed in an oven and heated in a range of 180° C. to 220° C. for approximately 5 to 30 minutes to bond the layers together. Additional details relating to useful bonding agents and their application to textile and non-textile surfaces may be found in U.S. Patent Application Publication No. 2003/0017775 and in U.S. Application Publication No. 2003/0139806, both of which are incorporated herein by reference. The devices of the present invention may be formed from single lamination techniques or multiple lamination techniques for multilayered devices. Further, lamination may be achieved without the use of adhesive through heat bonding techniques.

Figure 42:
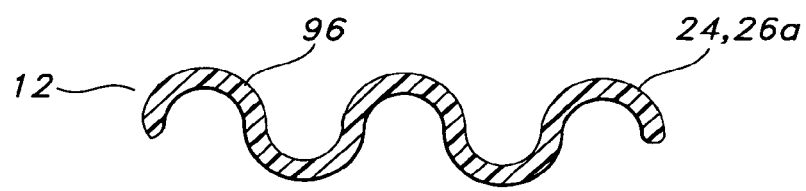
FIGS. 42 and 43 are cross-sectional views of the prosthesis of FIG. 4 taken along the B-B axis depicting a crimped prosthesis.
Figure 43:
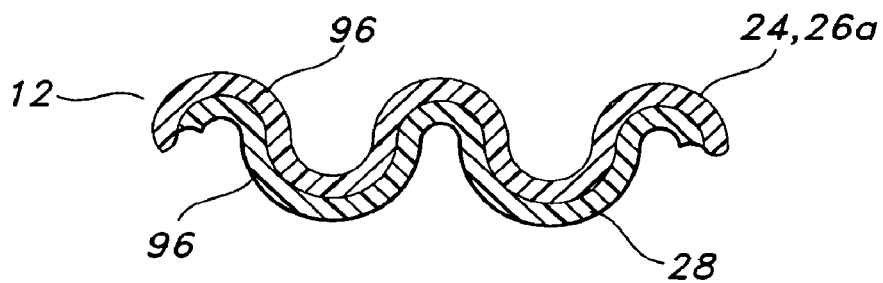

Moreover, the prosthesis 10 may be crimped along the tubular surface thereof to impart longitudinal compliance, kink resistance and enhanced handling characteristics. For example, as depicted in FIG. 42, the cylindrical wall 12 of prosthesis 10 may have a series of waves or crimps 96. The crimp may be provided by placing a coil of metal or plastic wire (not shown) around a stainless steel mandrel. The graft 10 is slid over the mandrel (not shown) and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart crimp 96 to the prosthesis 10. Further, as depicted in FIG. 43, the cylindrical wall 12 of prosthesis 10 having a textile portion, such as textile portion 24, 26a, and having a polymeric portion 28 may also be crimped, as described in U.S. Patent Application Publication No. 2003/0017775, the contents of which is incorporated herein by reference. Crimps 96 further provide increased longitudinal flexibility and structural integrity for prosthesis 10. For example, an uncrimped woven textile portion of the prosthesis 10 will typically have a longitudinal flexibility or longitudinal stretchability of less than about 10% over its quiescent length under a one-kilogram force or load. The crimped woven textile portion will have a longitudinal flexibility or stretchability from about 10% to about 100%. Desirably, the stretchability is from about 50% to about 100%, more desirably from about 70% to about 80%. A crimped woven textile portion of the prosthesis 10 will typically have a longitudinal flexibility or longitudinal stretchability of greater than about 10% over its quiescent length under a one-kilogram force or load.

Moreover, stent-graft 10 or graft 11 may be formed as an implantable prosthesis which is self-supporting and usable to maintain patency of a bodily vessel, such as in the coronary vasculature, esophagus, trachea, colon, biliary tract, urinary tract, prostate, tracheal/bronchial tubes and brain. Also, the textile portion 12 or the yarns forming textile portion 12 may be treated with any of the following therapeutic agents: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors);

anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides); vascular cell growth promoters (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous or vascoactive mechanisms.

Figure 44:
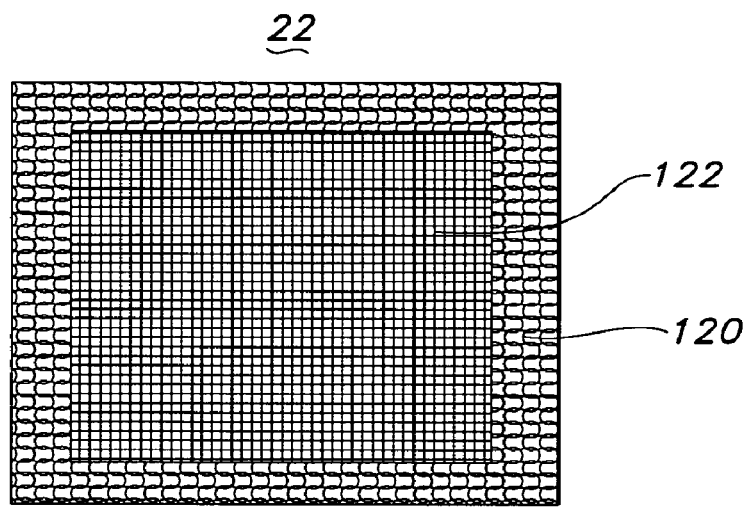
FIGS. 44 and 45 are top planar views of the patch of FIG. 3 depicting different textile portions thereat.
Figure 45:
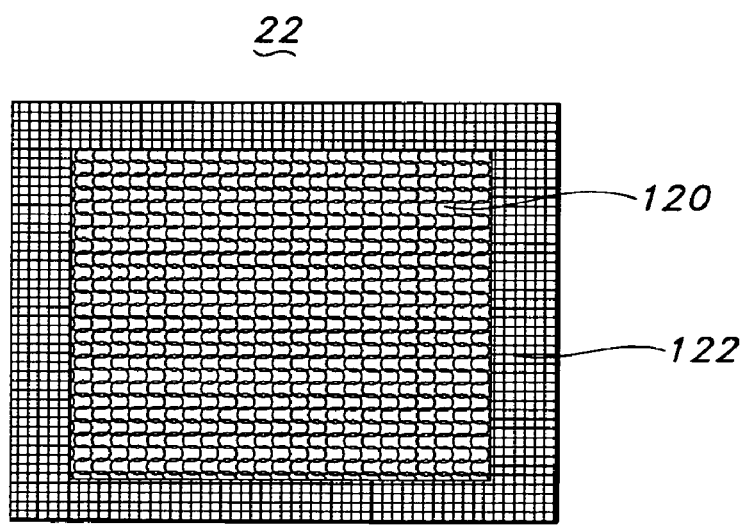

FIGS. 44 and 45 are top views of the medical patch 22 of FIG. 3. The patch 22 includes a knitted textile portion 120 and a woven textile portion 122. The different textile portions 120, 122 may be secured to one and the other by any of the above-described methods. Further, the patch 22 may also have a layer of PTFE or ePTFE (not shown) on one or both of its planar surfaces.

As depicted in FIG. 44, patch 22 may have an interior woven portion and a perimetrically disposed knitted portion. Alternatively, as depicted in FIG. 45, the interior portion may be knitted and the edge portions may be woven. The present invention is, however, not so limited and different arrangements of different textile portions may suitably be used.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What claimed is:

1. A stent/graft prosthesis comprising
   a seamless tubular knitted textile portion having yarns interloped in a knitted pattern defining a cylindrical knitted textile wall having opposed first and second open ends;
   a first seamless tubular woven textile portion having yarns interlaced in a woven pattern defining a cylindrical woven textile wall having opposed first and second open ends;
   an attachment means for securing said first open end of said first woven textile portion to said first open end of said knitted textile portion;
   a second seamless tubular woven textile portion having yarns interlaced in a woven pattern defining a cylindrical woven textile wall having opposed open ends, wherein said second woven textile portion is securably attached by said attachment means to said second open end of said knitted textile portion;
   a generally tubular stent having openings in its wall structure and having opposed first and second stent open ends, wherein said stent is circumferentially disposed about interior portions of said knitted textile and said woven textile walls; and
   a second attachment means for securing said stent about interior portions of said knitted textile and said woven textile walls.

2. The prosthesis of claim 1, wherein said woven portions have a permeability from about 30 to about 500 ml/mn/cm$^2$ of water at a pressure of 120 mm of mercury and said knitted portion has a permeability from about 30 to about 15,000 ml/min/cm$^2$ of water at a pressure of 120 mm of mercury.

3. The prosthesis of claim 1, wherein said woven portions have a resiliently longitudinal stretchability from about 10 to about 100 linear percent over its quiescent longitudinal dimension and said knitted portion has a resiliently longitudinal stretchability from about 5 to about 200 linear percent over its quiescent longitudinal dimension.

4. The prosthesis of claim 1, wherein said woven portions have a resiliently longitudinal stretchability of less than about 10 linear percent of its quiescent longitudinal dimension, and said knitted portion has a resiliently longitudinal stretchability from about 5 to about 200 linear percent over its quiescent longitudinal dimension.

5. The prosthesis of claim 1, further comprising a polymeric tube or layer circumferentially disposed and securably attached by said second attachment means about interior portions of said woven and said knitted textile walls.

6. The prosthesis of claim 1, wherein said stent is a radially distensible stent.

* * * * *